United States Patent

Shioiri

[11] Patent Number: 6,104,828
[45] Date of Patent: Aug. 15, 2000

[54] OPHTHALMOLOGIC IMAGE PROCESSOR

[75] Inventor: Takashi Shioiri, Paramus, N.J.

[73] Assignee: Kabushiki Kaisha Topcon, Tokyo, Japan

[21] Appl. No.: 08/216,842

[22] Filed: Mar. 24, 1994

[51] Int. Cl.[7] ........................................ G06K 9/00
[52] U.S. Cl. ............................ 382/128; 382/278; 351/206
[58] Field of Search ........................... 382/1, 6, 42, 117, 382/128, 130, 278, 294; 351/210, 206

[56] References Cited

U.S. PATENT DOCUMENTS

| | | | |
|---|---|---|---|
| 4,404,590 | 9/1983 | Mayer et al. | 348/129 |
| 4,715,703 | 12/1987 | Cornsweet et al. | 351/206 |
| 5,054,090 | 10/1991 | Knight et al. | 382/42 |
| 5,105,466 | 4/1992 | Tsujiuchi et al. | 382/1 |
| 5,218,648 | 6/1993 | Wells et al. | 382/1 |
| 5,220,360 | 6/1993 | Verdooner et al. | 351/212 |

Primary Examiner—Bhavesh Mehta
Attorney, Agent, or Firm—Finnegan, Henderson, Farabow, Garrett & Dunner, L.L.P.

[57] ABSTRACT

A medical image processor according to the present invention is used for analyzing eye fundus images 28 and 29, and comprises an image monitor capable of almost simultaneously displaying two images, a keyboard 23 for setting at least one reference point P1 to the eye fundus image 28, a mouse 24 for setting a correlation detection area Q to the other eye fundus image 29 with reference to the reference point P1, an image processing unit 21 for calculating a correlation between image information of the reference point P1 and image information of each point in the correlation detection area Q, and a system monitor 27 for displaying a result of the calculation made by the image processing unit 21 as a correlation table in which a vertical direction and a horizontal direction show position of each point in the detection area and which indicates the degree of correlation between the image information of the reference point and the image information of each point.

6 Claims, 7 Drawing Sheets

```
32 40 42 49 57 65 53 48 41 35 29
48 49 52 58 62 70 66 61 58 43 31
50 58 62 65 71 79 74 68 61 48 34
55 65 69 75 78 87 82 79 63 52 37
64 70 74 80 89 91 86 84 65 54 40
69 76 81 89 93*95*90 85 70 60 42
63 70 76 82 89 92 86 78 65 54 40
58 66 70 76 80 85 80 72 62 52 38
54 61 67 69 74 72 68 64 53 49 32
30 36 41 48 58 65 49 45 41 38 28
24 28 30 35 38 40 35 32 30 27 25
```

OPHTHALMOLOGIC IMAGE PROCESSOR

BACKGROUND OF THE INVENTION

1. Field of the Invention

This invention relates to an improvement of a medical image processor used for analyzing at least two comparison images which are obtained by simultaneously photographing an object such a fundus of an eye to be tested as a stereoscopic image or obtained by photographing the object at a different time as a time-lapsed image.

2. Prior Art

Heretofore, there is known a medical image processor used for analyzing at least two comparison images which are obtained by simultaneously photographing an object such a fundus of an eye to be tested as a stereoscopic image or obtained by photographing the object at a different time as a time-lapsed image.

A medical image processor of this type is used for analyzing a three-dimensional configuration of the eye fundus or changes of the eye fundus due to eye disease or the like.

In order to analyze a three-dimensional configuration of the eye fundus or changes of the eye fundus due to eye disease or the like, it is necessary to obtain a corresponding relation between a pair of comparison images. Heretofore, there is employed a method which will be described hereinafter, in order to obtain a corresponding relation between such pair of comparison images.

First, as shown in FIG. 1, a left image 1 and a right image 2 are simultaneously displayed, side by side, in a CRT monitor 3 as a pair of comparison images. Selected one of the images 1 and 2 is served as a reference image. Let us presume that the left image 1 has been selected as the reference image. Then, the operator sets a reference point K (positional ordinates X and Y) through a mouse or a keyboard. An easy spot for discrimination in the image is selected as this reference point K. Let us presume here that a branch spot between a blood vessel 4 and another blood vessel 5 in the left image 1 has been set as the reference point K. Thereafter, the operator sets a branch spot between a blood vessel 4' and another blood vessel 5' in the right image 2 as a corresponding point K' of the right image 2 corresponding to the reference point K by a mouse or a keyboard, while comparing the left image 1 with the right image 2.

Thus, there can be obtained a corresponding relation between the left image 1 and a right image 2. Three or more of such reference points K are usually set.

However, this conventional method has the problem in that it takes too long time to obtain a corresponding relation between the left image 1 and the right image 2. Since the left image 1 is compared with the right image 2 with naked eyes, a reproducible result is difficult to obtain and errors are substantially large. Moreover, since one of the images is sometimes seen in a somewhat distorted shape due to linearity characteristic of the CRT monitor 3, there exists errors originally in this method in which the left image 1 is compared with the right image 2 with naked eyes.

In the case of a three-dimensional measurement, this error is quite undesirable.

The reason is that in the case of a three-dimensional measurement, it is necessary to obtain an amount of displacement (disparity) of a picture element from the reference point. Height information (or depth information) is obtained with reference to the amount of displacement of the picture element from the reference point. Accordingly, if there exists an error at the time a corresponding relation is obtained between the left image 1 and the right image 2, this error results directly in error of the height information, thus making it difficult to perform a correct three-dimensional measurement. Moreover, in a stereoscopic photography, there is a fundamental difference in construction of an image between the left image 1 and the right image 2.

In addition, there is another problem in that the operator is required to pay too much attention (too much concentration).

In case of an analysis of the changes of the eye fundus due to eye disease or the like, the following procedure is taken.

As shown in FIGS. 2(A) and 2(B), an eye fundus image 7 as one of the comparison images is outputted as a hard copy 6 of a photograph or the like through a video printer. Then, a mark M serving as the reference point K is attached to the hard copy 6. Thereafter, only one or both of the comparison images are displayed in the CRT monitor 3. Then, while seeing the hard copy 6, the operator sets a corresponding point K' corresponding to the reference point K to the other eye fundus image 8 which is displayed in the CRT monitor 3 together with the eye fundus image 7. This method also involves the same problems as mentioned above. In FIG. 2(A), reference numeral 9 denotes a diseased spot.

SUMMARY OF THE INVENTION

It is therefore an object of the present invention to provide a medical image processor, in which a corresponding relation between a pair of comparison images can be obtained rapidly and easily, and a reproduction is assuredly obtainable.

To achieve the above object, there is essentially provided a medical image processor used for analyzing at least two comparison images which are obtained by simultaneously photographing an object such as an eye fundus as a stereoscopic image or obtained by photographing the object at a different time as a time-lapsed image, comprising means for almost simultaneously displaying the two comparison images; means for setting at least one reference point to one of the images; means for setting a correlation detection area to the other image with respect to the reference point; means for calculating a correlation between image information of the reference point and image information of each point in the detection area; and means for displaying a calculation result of the correlation calculation means as a correlation table in which the vertical direction and the horizontal direction show position of each point in the detection area and which indicate the degree of correlation between the image information of the reference point and the image information of each point in the detection area.

According to a medical image processor of the present invention, a pair of comparison images are almost simultaneously displayed in the monitor. The operator sets a reference point to one of the comparison images. By doing this, a detection area including the corresponding point is set to the other comparison image. The calculation means calculates or operates image information of the reference point and image information of each point in the detection area. The display means displays the result of calculation made by the correlation calculation means as a correlation table in which the vertical direction and the horizontal direction show position of each point in the detection area and which indicate the degree of correlation between the image information of the reference point and the image information of each point in the detection area.

DETAILED DESCRIPTION OF THE PREFERRED EMBODIMENT

A medical image processor according to one embodiment of the present invention will be described with reference to the accompanying drawings.

Figure 1:
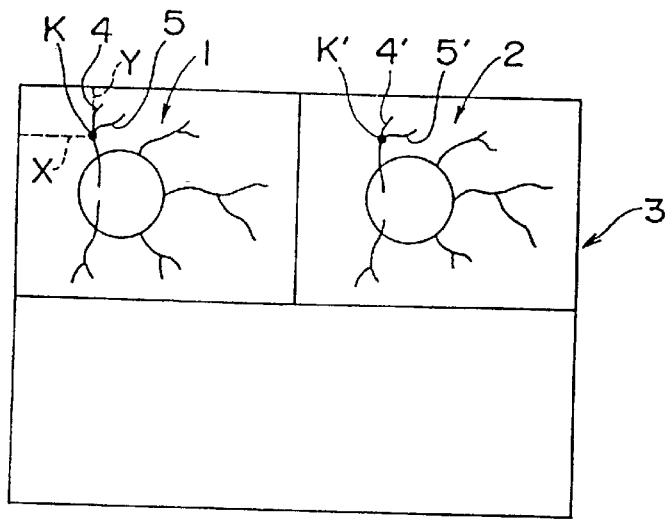
FIG. 1 is a schematic view for explaining how corresponding points can be given to the other image in accordance with the reference points in one image in a conventional manner.
Figure 2A:
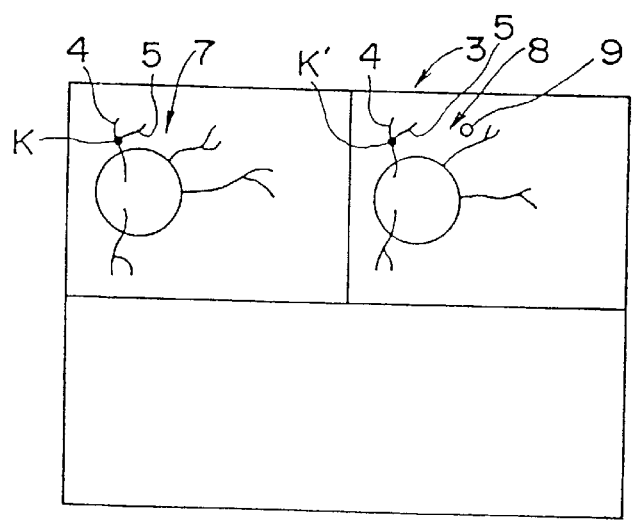
FIG. 2 is a schematic view like FIG. 1, but in which another conventional manner is shown.
Figure 2B:
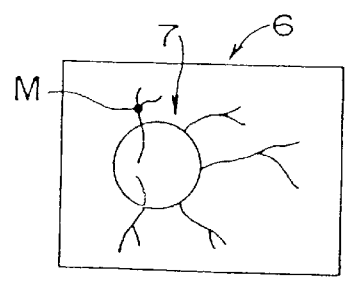
Figure 3:
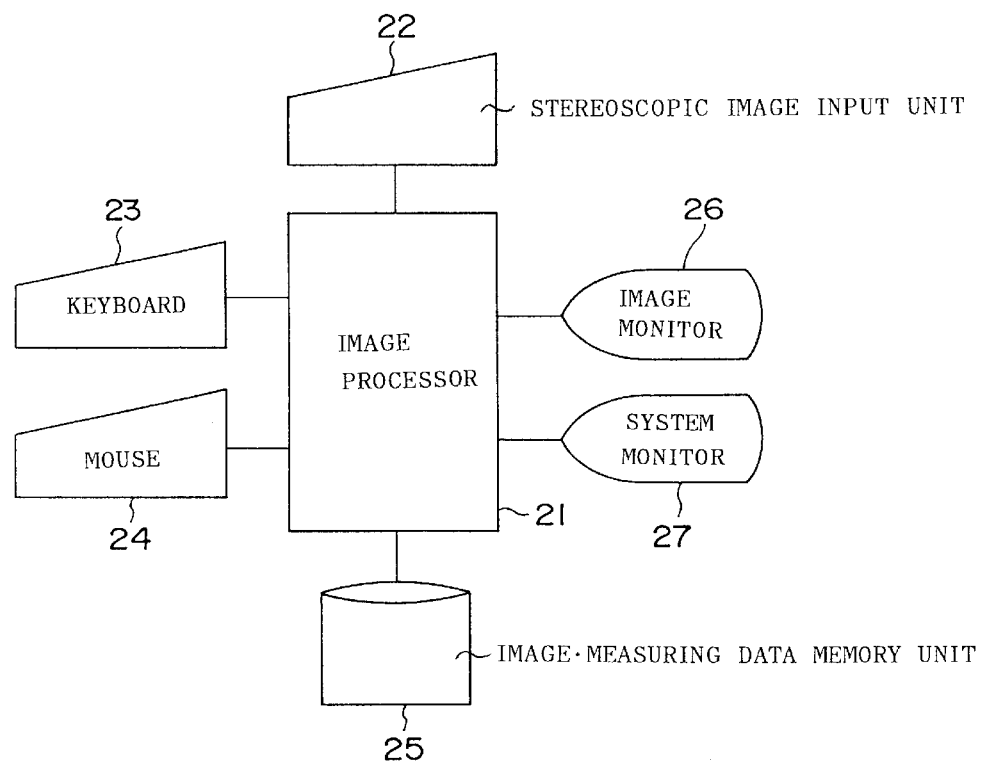
FIG. 3 is a system diagram of a medical image processor according to one embodiment of the present invention.

FIG. 3 is a system diagram of a medical image processor according to one embodiment of the present invention.

In this FIG. 3, reference numeral 21 denotes a stereo image processing unit which comprises a computer; 22, an image input unit; 23, a keyboard; 24, a mouse; 25, an image-measuring data memory unit; 26, an image monitor; 27, a system monitor, respectively. The stereo image input portion 22 is, for example, a CCD camera used as an eye fundus camera. In this case, a photographed stereoscopic image or a time-lapsed image photographed at a different time is inputted directly to the image processing unit 21 through the CCD camera. The image input unit 22 may be a slide input device or a scanner, for example. In that case, an eye fundus image of a stereoscopic eye fundus photograph and an eye fundus image showing time-lapsed changes in eye fundus photograph which is taken at a different time are digitally read in the image processing unit 21 by the slide input device or scanner.

The keyboard 23 and the mouse 24 are used for inputting commands for operating the image processing unit 21 or the like. The image processing unit 21 is used for performing various measuring processing in accordance with the image inputted. This image processing unit 21 is, for example, a personal computer or a work station. The image-measuring data memory unit 25 stores the inputted image and data relating to measurement such as a measured image, etc. In case of making a comparison of the changed images with the passage of time, it is a usual practice that the previously photographed eye fundus image is stored in the image-measuring data memory unit 25 as a digital data. As the image-measuring data 25, a hard disk and a photomagnetic disk are used, for example.

The image monitor 26 is used for displaying an inputted image, an image under processing and an image after processing. The system monitor 27 is used for instructing the input of commands to the image processing unit 1 and displaying data.

Figure 4:
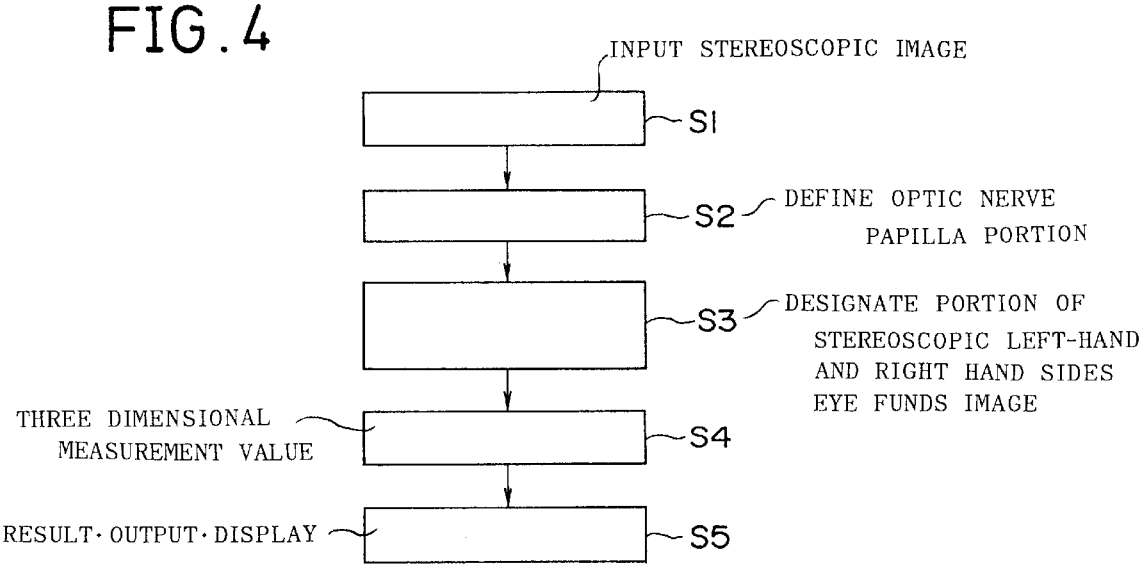
FIG. 4 is a flow chart for explaining the steps of operation of the medical image processor of FIG. 3.
Figure 6:
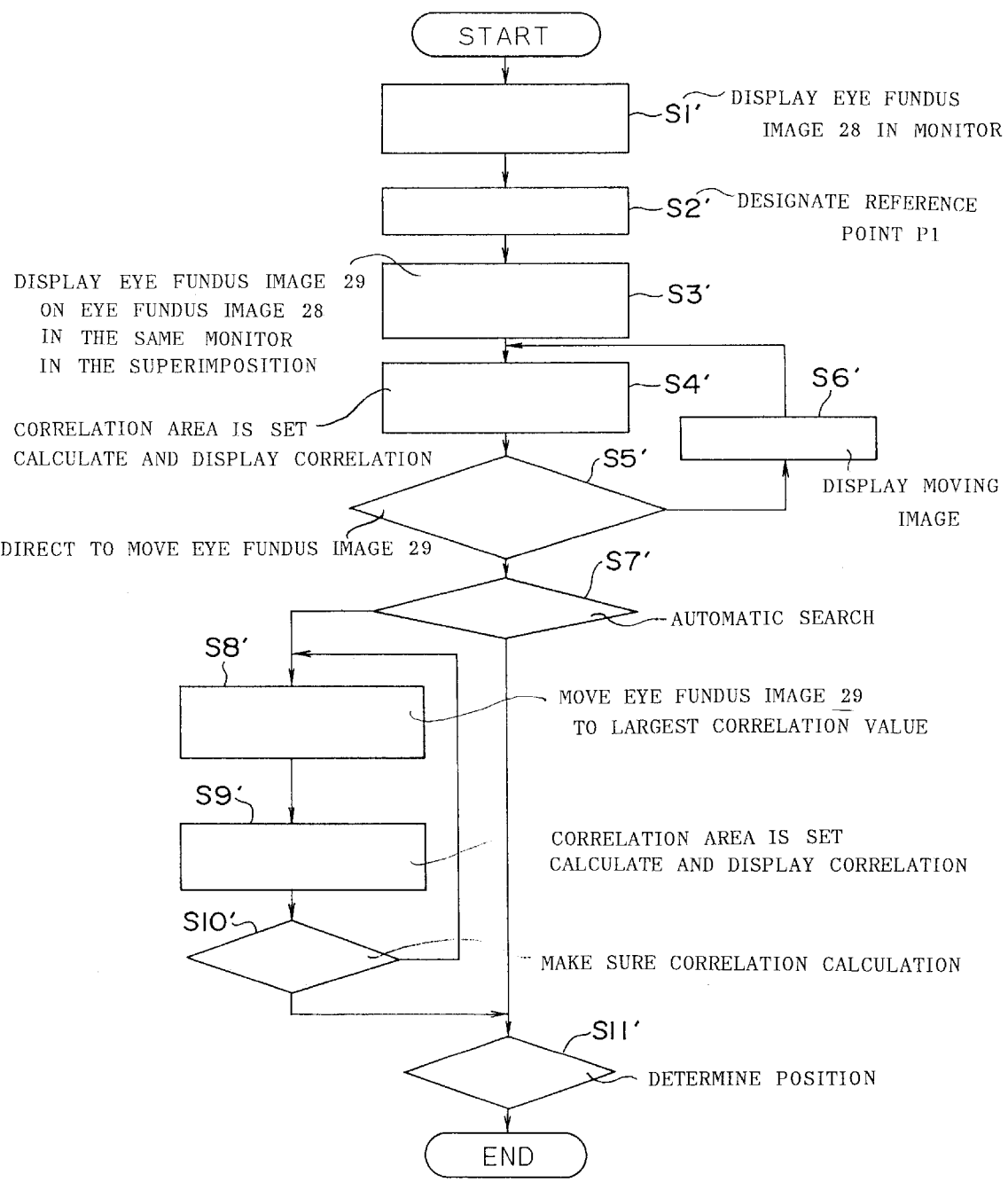
FIG. 6 is a flow chart for explaining an important portion of the present invention.

FIG. 4 shows an outline of a flow chart in which the present invention is applied to a three-dimensional measurement of an eye fundus image, and FIG. 6 is a flow chart for explaining the subject matter of the present invention.

Figure 5:
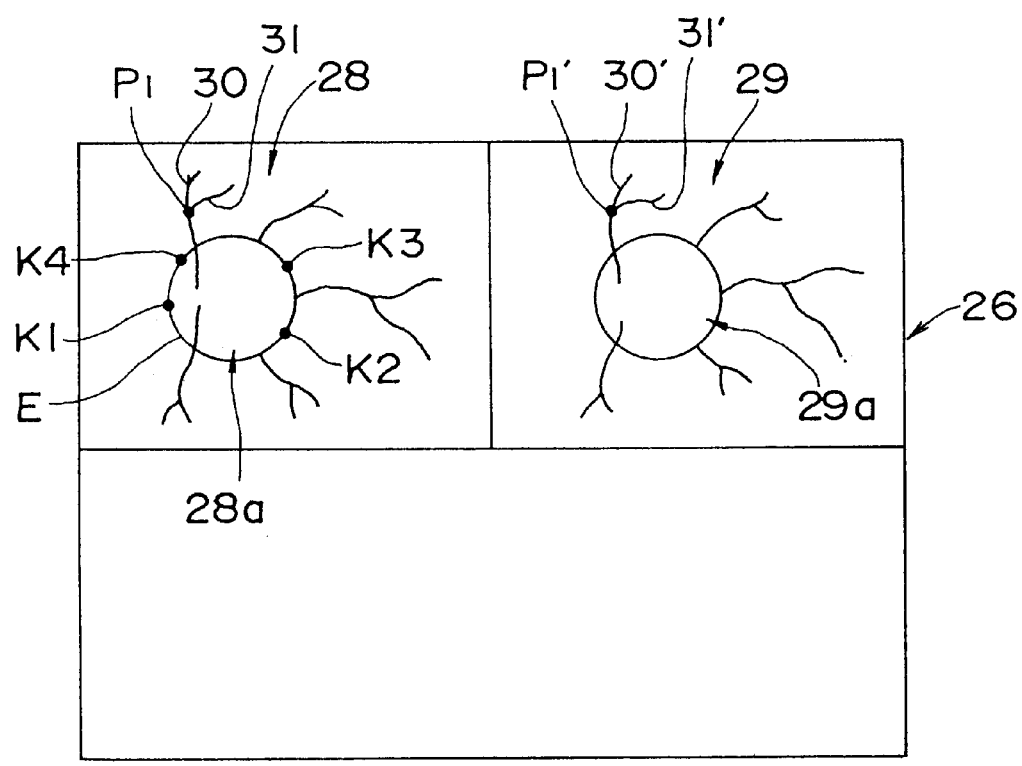
FIG. 5 is a view showing a displaying state before simultaneously displaying an eye fundus image in a superimposed relation.

First, the image processing unit 21 reads a stereoscopic image as a pair of comparison images (Step 1). This stereoscopic image is displayed in the image monitor 26. FIG. 5 shows a stereoscopic image which is displayed in the image monitor 26. In this FIG. 5, reference numeral 28 denotes a left-hand side eye fundus image, and 29; a right-hand side eye fundus image, respectively. Reference numerals 28a and 29a denote an optic nerve papilla portion. Subsequently, a configuration of optic nerve papilla portion 28a is defined, while looking the left-hand side eye fundus image 28 which is displayed in the image monitor 26 in order to obtain a value (Step 2). The operator designates, for example, four points K1, K2, K3 and K4 on the optic nerve papilla portion 28a in all directions. The image processing unit 21 obtains a single number of ellipse E in accordance with these four points K1, K2, K3 and K4. By doing this, the configuration of optic nerve papilla portion for measurement processing is defined. Then, the position of the eye fundus image 28 is brought into alignment with that of the other eye fundus image 29 (Step 3). This positional alignment will be described in detail later.

The stereoscopic image can be obtained by photographing the same eye fundus image from opposite sides at a predetermined angle. Accordingly, the position of a particular part of the left-hand side eye fundus image 28 and the position of a particular part of the right-hand side eye fundus image 29 are positionally displaced relative to each other. Therefore, in Step 4, the relative displacement amount of the right-hand side eye fundus image 29 is found with reference to the left-hand side eye fundus image 28. With reference to the amount of displacement thus obtained, there can be obtained a three dimensional measurement value as height information (or depth information).

The three dimensional measurement value obtained in Step 4 is displayed in the image monitor 26 together with measurement parameters (Step 5).

Next, the details of the positional alignment will be described with reference to the flow chart of FIG. 6.

As shown in FIG. 5, the left-hand side eye fundus image 28 and the right-hand side eye fundus image 29 are displayed, side by side, in the image monitor 26 (Step 1'). Subsequently, the operator inputs the reference point P1 to a properly selected position of the eye fundus image 28 (Step 2'). This reference point P1 is preferably a peculiar part like a branch point for a blood vessel 30 and another blood vessel 31. The reference point P1 is designated by a mark such as □, ○, x, or the like. The reason why these marks are used for designation is that in this way, the position of the reference point P1 can be clearly recognized for the operator.

Figure 7:
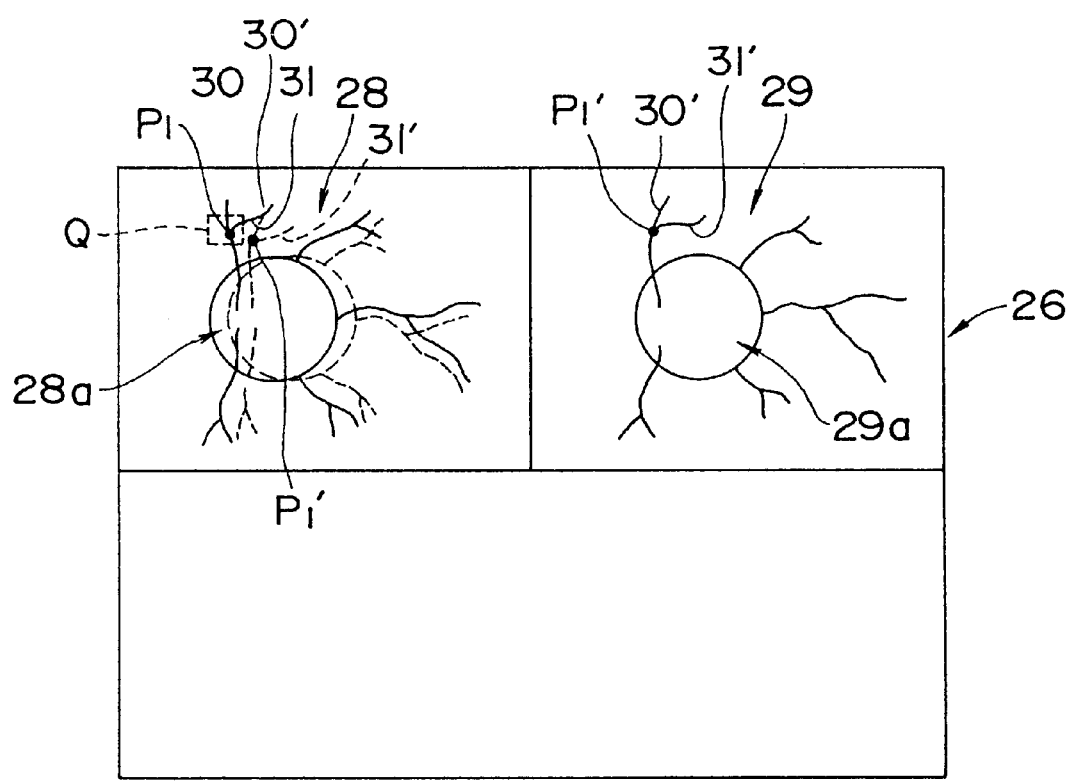
FIG. 7 is a view showing a state in which a detection area is set and an eye fundus image is simultaneously displayed in a superimposed relation.

As shown in FIG. 7, the operator almost displays the eye fundus image 29 on the eye fundus image 28 in the same monitor screen area (Step 3') in the superimposition. In FIG. 7, the eye fundus image 29 is shown by broken lines.

Different colors are employed for the eye fundus images 28 and 29, respectively. The color of the eye fundus image 28 is preferably in a complemental relation to that of the other eye fundus image 29. For example, if the eye fundus image 28 is displayed in green color and the other eye fundus image 29 in red color, the overlapped image portion looks yellow. The displaced portion looks green and red separately. Therefore, a corresponding point P1' of the eye fundus image 29 corresponding to the reference point P1 of the eye fundus image 28 can easily be found. Here, the corresponding point P1' shows a branch point between the blood vessel 30' and the blood vessel 31' in the image 29.

It is also possible that the eye fundus images 28 and 29 are displayed in the image monitor 26 by switching alternately. In that case, the image portion where the eye fundus 28 and the other eye fundus 29 are overlapped looks still owing to the after-image phenomenon. On the other hand, the displaced portion between the eye fundus images 28 and 29 looks flickering. Owing to this feature, the corresponding point P1' of the eye fundus image 29 corresponding to the reference point P1 of the eye fundus 28 can easily be found. In other words, the positional displacement between the eye fundus image 28 and the other eye fundus image 29 can be finely adjusted.

It is desirable that the switching speed of the display between the eye fundus images 28 and 29 is variable. For example, it is possible to make a display switching twice to ten times per second in accordance with the operator's instructions.

However, it is difficult to identify the reference point P1' of the eye fundus image 29 corresponding to the reference point P1 of the eye fundus image 28 because of difference in structure.

Therefore, in order to obtain the corresponding point P1' of the eye fundus image 29 corresponding to the reference point P1 of the eye fundus image 28, the image processing unit 21 calculates a correlation. The image processing unit 21 sets a detection area Q including the reference point P1, first. This detection area Q is shown on an enlarged scale in FIG. 8.

This detection area Q is a regular square consisting of 11×11 picture elements. However, the size of the detection area may properly be selected. That is, it may be any of 13×13, 15×15, 9×9, 7×7, or the like, all in picture elements.

Figures 8, 9:
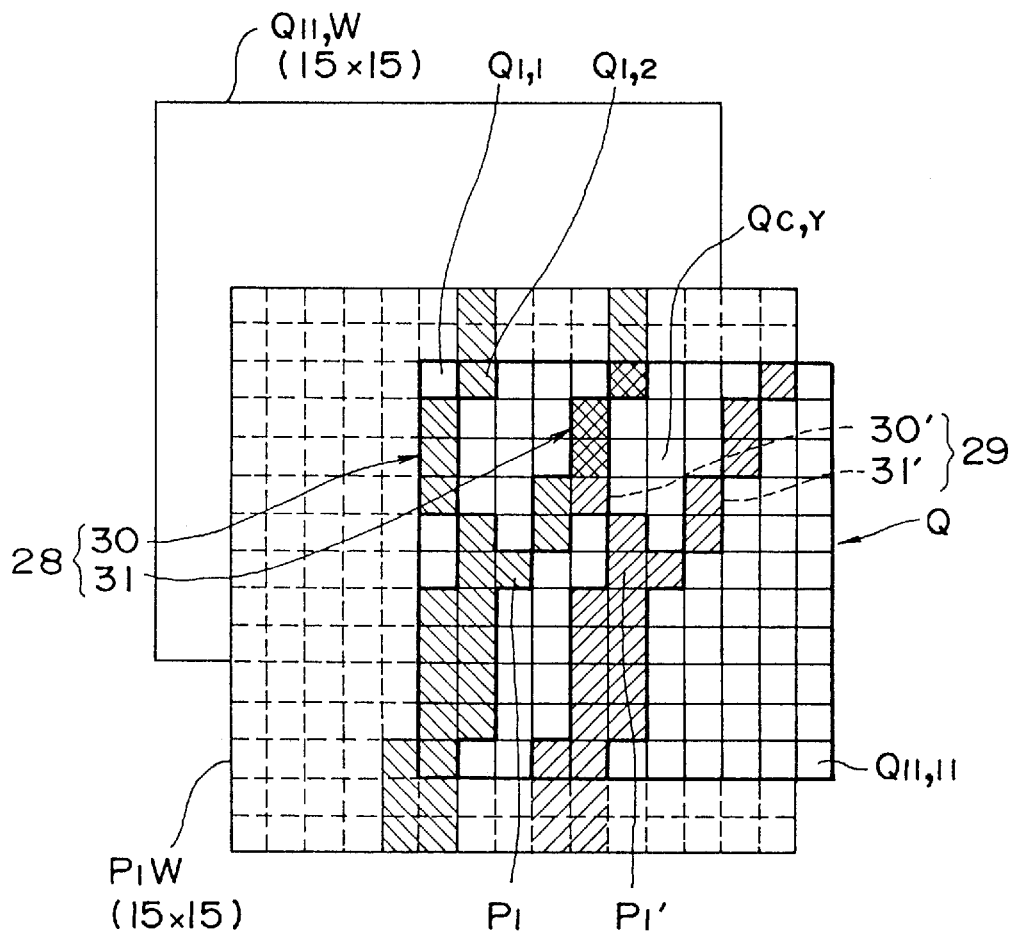
FIG. 8 is an enlarged schematic view of the detection area showing a state in which the correlation degree is low.
FIG. 9 is a table showing one example of a result of a correlation calculation.

As shown on an enlarged scale in FIG. 8, the correlation is considered to be low when the positional displacement between the eye fundus images 28 and 29 are great. The correlation numerical value table is displayed in the system monitor 27 (see FIG. 9, FIG. 11) by image processing unit 21. In the correlation numerical value table, the vertical direction and the horizontal direction show position of each point in the detection area Q. The numerical values show the degree of correlation between the image information of the reference point P1 and the image information of each point in the detection area.

FIG. 9 shows the correlation numerical value table 32. This correlation numerical value table is made in the manner as will be described hereinafter.

That is, with respect to one image including the reference point P1 and the other image including the detection area Q, we set a regular square window (for example, 15×15 picture elements) P1W with centering reference point P1 and windows QcrW with centering each point Qcr included in the detection area Q. The window QcrW is the same size as the window P1W. (c and r represent integer values, respectively, indicating the line and the row. In case the detection area Q consists of 11×11 picture elements as shown in FIG. 8, c represents an integer value from 1 to 11, and r represents an integer value from 1 to 11). Then, a correlation between the window P1W and the window QcrW is calculated. The correlation between the window Q1,1W (15×15 picture elements) which has a picture element Q1,1 in center and the window P1W (15×15 picture elements) are which has a reference point P1 in center shown, in FIG. 8. If one of the windows QcrW is the same (for example, branch of the blood vessel) as the P1W and has the same condition (the term "condition" used here includes the meaning of direction and size), the density patterns of local images inside the two windows P1W and QcrW should be equal. At this time, a normal correlation Cn=1.

This normalized correlation Cn can be obtained in accordance with the expression shown below.

$$Cn = \frac{\sum (Xn - Xm)(Yn - Ym)}{[\sum (Xn - Xm)^2 \sum (Yn - Ym)^2]^{1/2}}$$

In the above expression, reference characters Xn and Yn represent density values of the images in the respective windows P1W and QcrW, and Xm and Ym represent average values of them. n is an integral number from 1 to 15. In case the density values Xn and Yn are fully in agreement, the normalized correlation Cn=1. In case of inversion, Cn=−1. In case of non-correlation, Cn=0. The correlation numerical value table of the detection area Q indicates 100 times of the values obtained by this normalized correlation with respect to respective points (respective picture elements) of the windows P1W and QcrW. Each correlation numerical value table can be obtained for each point Qcr of the detection area Q (11×11 picture elements).

Aside from the normalized correlation method, there can be employed a cross correlation method, a correlation method for obtaining a sum of absolute values of a remainder, and a correlation method for obtaining a square sum of a remainder, in order to evaluate the correlation between the eye fundus image 28 and the other eye fundus image 29.

As shown in FIG. 9, a value of a corresponding point having the largest correlation is affixed with * marks on both sides thereof (Step 4').

Figures 10, 11:
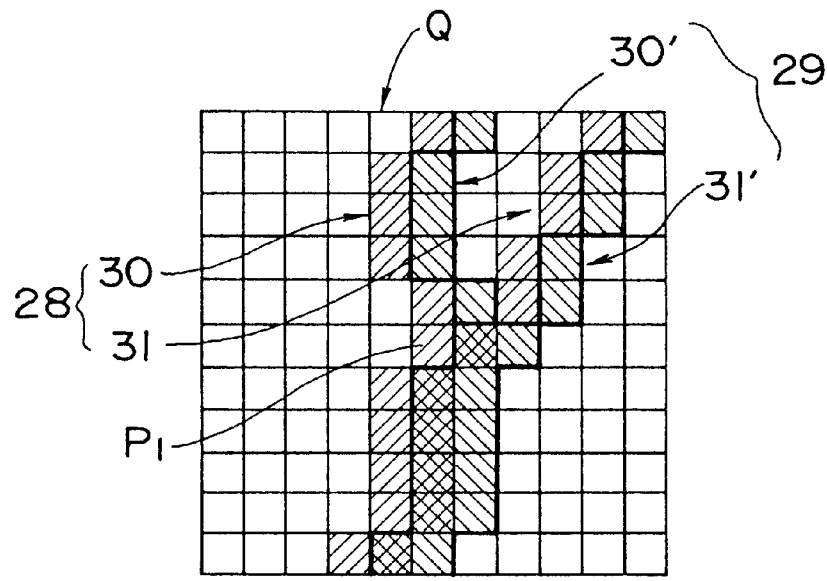
FIG. 10 is an enlarged schematic view of the detection area showing a state in which the correlation degree is high.
FIG. 11 is a table showing another example of a result of a correlation calculation.

The operator moves the eye fundus image 29 such that the largest value (numerical value affixed with * mark on both sides thereof) of the correlation numerical values comes to the center. Then, the image processing unit 21 moves the eye fundus image 29 so as to be superimposed on the eye fundus image 28 (Step 6'). FIG. 10 shows an enlarged view of the obtained detection area Q for such obtained eye fundus images 28 and 29. In case the positional difference between the eye fundus 28 and the other eye fundus 29 is small like this, the correlation is considered to be high.

The image processing unit 21 evaluates the correlation between the eye fundus 28 and the other eye fundus 29 again (Step 4'). Let us presume that a correlation numerical value table 32' as shown in FIG. 11 has been obtained through the above procedure. The operator determines the corresponding point P1' with reference to this result.

For an automatic search, the operator operates the automatic search key in Step 7' (Step 7').

In case the automatic search key is not operated, it goes to Step 11″ where the corresponding point P1' corresponding to the reference point P1 is determined. In case the automatic key has been operated, it goes to Step 8'.

The image processing unit 21 moves the eye fundus image 29 such that the largest correlation value can be obtained between the eye fundus 28 and the other eye fundus 29 (Step 8'). Subsequently, the image processing unit 21 executes the same correlation calculation as in Step 4' (Step 9'). Then, the image processing unit 21 makes sure and evaluates the result (Step 10'). Thereafter, the image processing unit 21 automatically moves the eye fundus image 29 such that the correlation numerical value table becomes the largest.

The image processing unit 21 repeats the procedure from Step 8' to Step 10', and determines the position where the correlation numerical value table becomes the largest (Step 11').

If this correlation table is used, it is effective for diagnosis of glaucoma, etc.

The medical image processor according to the present invention can rapidly and easily obtain a corresponding relation between a pair of comparison images and assure a reproduction.

Moreover, means for storing information of said reference point, and a function for automatically setting the information of said reference point thus stored as a new analysis reference point.

What is claimed is:

1. A medical image processor for correlating and analyzing at least two comparison images, comprising:

means for substantially simultaneously displaying said two comparison images;

means for setting at least one reference point in one of the images;

means for setting a correlation detection area related to said at least one reference point in the other image;

means for obtaining and calculating a degree of correlation between image information of said at least one reference point and image information of each point in said detection area;

means for displaying a plurality of numerical values representing the degree of correlation in a rectangular correlation table, the plurality of said numerical values being arranged in a one-to-one correspondence with respect to each point in the detection area;

image movement means for relatively moving said two comparison images so that the image information of said at least one reference point coincides with image information of a corresponding point represented by a maximum numerical value in said correlation table, said means for obtaining and calculating a degree of correlation and said image movement means being operable alternately and repeatedly; and decision means for deciding a coincidence between the image information of said reference point and the image information of the corresponding point.

2. The medical image processor according to claim 1 wherein the at least two comparison images are obtained by simultaneously photographing an object such as an eye fundus as a stereoscopic image.

3. The medical image processor according to claim 1 wherein the at least two comparison images are obtained by photographing an object such as an eye fundus at a different time as a time-lapsed image.

4. The medical image processor according to claim 1 wherein the maximum numerical value is displayed on the display means in a special manner with respect to other numerical values in the correlation table.

5. The medical image processor according to claim 1 wherein said one comparison image and the other image are alternately displayed in order to visually recognize the degree of correlation between the two images.

6. The medical image processor according to claim 1 wherein the comparison images are displayed in complementary colors.

* * * * *